(12) United States Patent
Shute et al.

(10) Patent No.: US 12,721,572 B2
(45) Date of Patent: Sep. 1, 2026

(54) MANAGING AN OPERATING MODE OF A WEARABLE HEALTH MONITOR

(71) Applicant: Cardiac Pacemakers, Inc., St Paul, MN (US)

(72) Inventors: Jonathan B. Shute, Eagan, MN (US); Bin Mi, Arden Hills, MN (US); Jeffrey S. Rotter, Rochester, MN (US); Gale G. McFarland, Sioux Falls, SD (US); Michael Thomas Edward McRoberts, Mazeppa, MN (US); Timothy J. Alpers, Rochester, MN (US); Brian Kronstedt, Edina, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 323 days.

(21) Appl. No.: 18/227,170

(22) Filed: Jul. 27, 2023

(65) Prior Publication Data

US 2024/0057940 A1 Feb. 22, 2024

Related U.S. Application Data

(60) Provisional application No. 63/399,284, filed on Aug. 19, 2022.

(51) Int. Cl.
*A61B 5/00* (2006.01)
*A61B 5/0205* (2006.01)
(Continued)

(52) U.S. Cl.
CPC ........ *A61B 5/6844* (2013.01); *A61B 5/02055* (2013.01); *A61B 5/352* (2021.01); *A61B 7/00* (2013.01); *A61B 5/02416* (2013.01)

(58) Field of Classification Search
CPC ... A61B 5/6843; A61B 5/0002; A61B 5/0205; A61B 5/0531; A61B 5/1032;
(Continued)

(56) References Cited

U.S. PATENT DOCUMENTS

2012/0317430 A1* 12/2012 Rahman ............... A61B 5/7455 713/323
2015/0135310 A1* 5/2015 Lee ......................... G06F 1/163 726/20

(Continued)

FOREIGN PATENT DOCUMENTS

WO WO-2020178746 A1 * 9/2020 .......... A61M 16/203

OTHER PUBLICATIONS

International Search Report and Written Opinion received for PCT Patent Application No. PCT/US2023/028856, mailed on Nov. 8, 2023, 9 pages.

*Primary Examiner* — Sana Sahand
(74) *Attorney, Agent, or Firm* — Faegre Drinker Biddle & Reath LLP

(57) ABSTRACT

A method includes obtaining test criteria for a monitor configured to be attached to a user; obtaining reference data; determining, based on the test criteria and the reference data, a detached state of the monitor. The determining the detached state includes performing a set of tests indicated in the test criteria. The set of tests includes a first test corresponding to a first power consumption by the monitor; and a second test different from the first test. The second test corresponds to a second power consumption by the monitor, and the second power consumption is larger than the first power consumption. The method further includes automatically modifying, in response to the determining the detached state, an operating mode of the monitor.

20 Claims, 8 Drawing Sheets

(51) Int. Cl.
*A61B 5/352* (2021.01)
*A61B 7/00* (2006.01)
*A61B 5/024* (2006.01)

(58) Field of Classification Search
CPC ... A61B 5/1116; A61B 5/6833; A61B 5/6835; A61B 5/024; A61B 5/7221; A61B 5/4806; A61B 2562/0271; A61B 2562/06; A61B 2562/08; A61B 2562/0257; A61B 2562/0219
See application file for complete search history.

(56) References Cited

U.S. PATENT DOCUMENTS

2017/0038848 A1 2/2017 Yuen et al.
2020/0367816 A1 11/2020 Panneer Selvam
2021/0052198 A1* 2/2021 Parvaneh .............. A61B 5/1117
2022/0103915 A1 3/2022 Yoshida et al.

* cited by examiner

MANAGING AN OPERATING MODE OF A WEARABLE HEALTH MONITOR

CROSS REFERENCE TO RELATED APPLICATION

This application claims priority to Provisional Application No. 63/399,284, filed Aug. 19, 2022, which is herein incorporated by reference in its entirety.

TECHNICAL FIELD

The present disclosure relates to devices, methods, and systems for managing an operating mode of a wearable health monitor.

BACKGROUND

Wearable health monitors can include devices having sensing and measuring components that can monitor health parameters and/or conditions of a user. For example, wearable health monitors can include mobile devices worn by patients to monitor cardiac data, blood pressure data, and/or blood sugar data. Such data can be collected over time and provided to medical professionals for treatment.

SUMMARY

In Example 1, a method includes obtaining test criteria for a monitor configured to be attached to a user; obtaining reference data; determining, based on the test criteria and the reference data, a detached state of the monitor. The determining the detached state includes performing a set of tests indicated in the test criteria. The set of tests includes a first test corresponding to a first power consumption by the monitor; and a second test different from the first test, the second test corresponding to a second power consumption by the monitor, the second power consumption being larger than the first power consumption. The method further includes automatically modifying, in response to the determining the detached state, an operating mode of the monitor.

In Example 2, the method of Example 1, wherein the reference data comprises a threshold impedance, and wherein performing the first test comprises: obtaining, by an impedance sensor of the monitor, impedance data; and comparing the impedance data to the threshold impedance.

In Example 3, the method of Example 1, wherein performing the second test is in response to determining that the impedance data does not exceed the threshold impedance.

In Example 4, the method of Example 3, wherein the reference data further includes a threshold temperature, and wherein the performing the second test includes: obtaining, by a temperature sensor of the monitor, temperature data, and comparing the temperature data to the threshold temperature data.

In Example 5, the method of Example 3, wherein the set of tests comprises a third test different from the first test and different from the second test, wherein the third test corresponds to a third power consumption by the monitor, and wherein the third power consumption is larger than the second power consumption.

In Example 6, the method of Example 5, wherein the performing the third test is in response to determining that the temperature data does not exceed the threshold temperature data.

In Example 7, the method of Example 5, wherein the reference data comprises threshold PPG data, and wherein performing the third test includes: obtaining, by a light sensor of the monitor, PPG data, and comparing the PPG data to the threshold PPG data.

In Example 8, the method of Example 2, wherein the reference data comprises threshold R wave data, and wherein performing the second test includes: obtaining, by the monitor, R wave data, and comparing the R wave data to the threshold R wave data.

In Example 9, the method of Example 2, wherein the reference data comprises threshold heart sound data, and wherein performing the second test includes: obtaining, by an accelerometer of the monitor, heart sound data, and comparing the heart sound data to the threshold heart sound data.

In Example 10, method of Example 9, wherein the heart sound data comprises a signal strength index, and wherein the method further comprises determining that the signal strength index does not exceed the threshold heart sound data.

In Example 11, the method of any Examples 1 to 10, 11, wherein the automatically modifying the operating mode of the monitor comprises changing the operating mode from an active mode to a passive mode.

In Example 12, the method of any examples 1 to 11, 12, further comprising: issuing a notification to the user; and receiving, in response to issuing the notification, a verification of the detached state.

In Example 13, a computer program product comprising instructions to cause one or more processors to carry out the operations of the method of Examples 1-12.

In Example 14, a computer-readable medium having stored thereon the computer program product of Example 13.

In Example 15, a computer comprising the computer-readable medium of Example 14.

In Example 16, a cardiac monitor includes a cardiac sensor, a processor, and memory that stores computer-executable instructions for causing the processor to: determine, based on test criteria and reference data, whether the cardiac monitor is in an attached state or a detached state by carrying out (1) a first test corresponding to a first power consumption by the cardiac monitor and (2) a second test different from the first test and corresponding to a second power consumption by the cardiac monitor. The second power consumption is larger than the first power consumption. The instructions further cause the processor to automatically modify, in response to the determining the detached state, an operating mode of the monitor.

In Example 17, the cardiac monitor of Example 16, wherein the cardiac sensor comprises an electrocardiogram sensor.

In Example 18, the cardiac monitor of Example 16, further comprising an impedance sensor, wherein the reference data comprises a threshold impedance, and wherein the first test comprises (1) obtaining impedance data from the impedance sensor and (2) comparing the impedance data to the threshold impedance.

In Example 19, the cardiac monitor of Example 18, the second test is carried out in response to a determination that the impedance data does not exceed the threshold impedance.

In Example 20, the cardiac monitor of Example 19, further comprising a temperature sensor, wherein the reference data further comprises a threshold temperature, and the second test comprises (1) obtaining temperature data from the temperature sensor and (2) comparing the temperature data to the threshold temperature data.

In Example 21, the cardiac monitor of Example 16, wherein the memory further stores computer-executable instructions for causing the processor to carry out a third test corresponding to a third power consumption by the cardiac monitor, wherein the third power consumption is larger than the second power consumption.

In Example 22, the cardiac monitor of Example 21, wherein the third test is carried out in response to a determination that temperature data does not exceed a threshold temperature.

In Example 23, the cardiac monitor of Example 21, further comprising a light sensor, wherein the reference data comprises threshold PPG data, wherein the third test comprises obtaining PPG data from the light sensor and comparing the PPG data to the threshold PPG data.

In Example 24, the cardiac monitor of Example 16, wherein the reference data comprises threshold R wave data, wherein the second test comprises obtaining R wave data from the cardiac sensor and comparing the R wave data to the threshold R wave data.

In Example 25, the cardiac monitor of Example 16, further comprising an accelerometer, wherein the reference data comprises threshold heart sound data, and wherein the second test comprises obtaining heart sound data from the accelerometer of the monitor and comparing the heart sound data to the threshold heart sound data.

In Example 26, the cardiac monitor of Example 25, wherein the heart sound data comprises a signal strength index, and wherein the second test comprises determining that the signal strength index does not exceed the threshold heart sound data.

In Example 27, the cardiac monitor of Example 16, wherein the automatically modifying the operating mode comprises changing the operating mode from an active mode to a passive mode.

In Example 28, the cardiac monitor of Example 16, wherein the memory further stores computer-executable instructions for causing the processor to issue a notification to a user and receive, in response to issuing the notification, a verification of the detached state.

In Example 29, a method includes obtaining test criteria for a monitor configured to be attached to a user; and obtaining reference data; determining, based on the test criteria and the reference data, a detached state of the monitor. Determining the detached state includes performing a set of tests indicated in the test criteria. The set of tests include a first test corresponding to a first power consumption by the monitor and a second test different from the first test. The second test corresponds to a second power consumption by the monitor, and the second power consumption is larger than the first power consumption. The method further includes automatically modifying, in response to the determining the detached state, an operating mode of the monitor.

In Example 30, the method of Example 29, wherein the reference data comprises a threshold impedance, and wherein performing the first test includes obtaining, by an impedance sensor of the monitor, impedance data. The first test also includes comparing the impedance data to the threshold impedance.

In Example 31, the method of Example 30, wherein performing the second test is in response to determining that the impedance data does not exceed the threshold impedance.

In Example 32, the method of Example 31, wherein the reference data further comprises a threshold temperature, and wherein the performing the second test includes obtaining, by a temperature sensor of the monitor, temperature data. The second test further includes comparing the temperature data to the threshold temperature data.

In Example 33, the method of Example 31, wherein the set of tests comprises a third test different from the first test and different from the second test. The third test corresponds to a third power consumption by the monitor, and the third power consumption is larger than the second power consumption.

In Example 34, the method of Example 33, wherein the performing the third test is in response to determining that the temperature data does not exceed the threshold temperature data.

In Example 35, the method of Example 29, wherein the automatically modifying the operating mode of the monitor comprises changing the operating mode from an active mode to a passive mode.

In Example 36, a cardiac monitor comprising the computer program product, the computer-readable medium, and/or the computer of Examples 13-15.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

Figure 1:
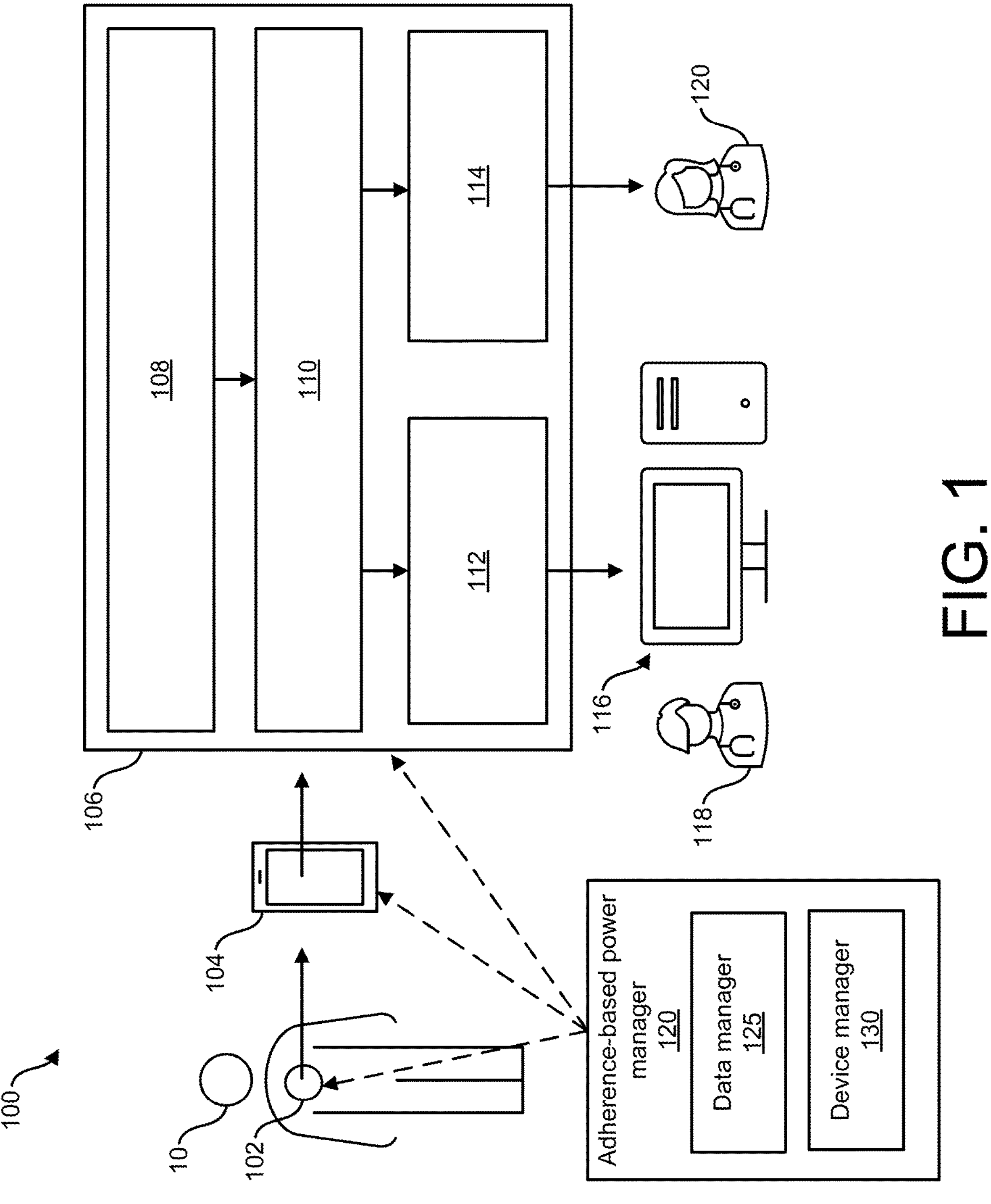
FIG. 1 shows a computing environment including an adherence-based power manager, server, remote computer, and user interface, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to wearable health monitors and particularly to aspects involving managing an operating mode of a wearable health monitor. While the present disclosure is not necessarily limited to such applications, various aspects of the disclosure may be appreciated through a discussion of various examples using this context.

A wearable health monitor can be worn by a user, such as a patient, to monitor one or more health parameters and/or conditions. A cardiac monitor, such as a patch-based electrocardiogram ("ECG") sensor, is an example of such a wearable health monitor. In an example, a patch-based ECG sensor can be attached to a patient's body to acquire data that can be used to determine whether the patient has experienced a cardiac event. In some instances, such a patch-based ECG sensor can wirelessly transmit the acquired data to a medical professional treating the patient.

In certain instances, a wearable health monitor can be attached, de-attached, and reattached to a user. Proper attachment of a wearable health monitor to a user can significantly affect the integrity of data it acquires. Accordingly, accurately determining an attachment state of a wearable health monitor (e.g., determining whether a wearable health monitor is attached or detached) can be a priority. Additionally, in some instances, a wearable health monitor can have an active mode and a passive mode. For example, an active mode can include a configuration in which one or more sensors of the wearable health monitor are powered on and are operating to collect data. A passive mode can include a configuration in which the one or more sensors are powered off or are in a low-power mode and are not operating to continuously collect data. Thus, the wearable health monitor can consume more power in the active mode than it does in the passive mode. Accordingly, managing the operating mode of the wearable health monitor can be an additional priority. Managing the operating mode such that the wearable health monitor is in an active mode when it is properly attached to a user and in a passive mode when it is detached from a user can provide efficient power consumption by the wearable health monitor.

Determining whether a wearable health monitor is attached or detached can present challenges. In some instances, a user can neglect to manually indicate an attachment state of a wearable health monitor. Additionally, in some instances, employing sensors of a wearable health monitor to determine its attachment state can unduly burden its power supply. Further, in some instances, employing tools to analyze data of a wearable health monitor to determine its attachment state can excessively consume resources of one or more computer systems. Thus, there is a need to accurately and efficiently determine an attachment state of a wearable health monitor and to manage an operating mode of the wearable health monitor based on the attachment state.

To address these and other challenges, instances of the present disclosure include an adherence-based power manager ("ABPM"). In certain instances of the present disclosure, the ABPM can employ tiered testing to automatically determine an attachment state of a wearable health monitor. Tiered testing can include the ABPM automatically performing a sequence of tests to determine the attachment state of the wearable health monitor. The sequence of tests can begin with a first test corresponding to a lowest quantity of power (i.e., electrical power) consumed by the wearable health monitor. The sequence can further include subsequent tests by the ABPM, during which, the wearable health monitor can consume increasing quantities of power. For example, tiered testing can include the wearable health monitor consuming a first quantity of power during a first test by the ABPM; consuming a second quantity of power during a second test by the ABPM; and consuming a third quantity of power during a third test by the ABPM. In this example, the second quantity of power can be larger than the first quantity of power, and the third quantity of power can be larger than the second quantity of power. In certain instances, such tiered testing can facilitate efficient power consumption by the wearable health monitor as the ABPM determines an attachment state. Furthermore, in some instances, such tiered testing can include redundant tests that provide improved accuracy in determining the attachment state of the wearable health monitor. In certain instances of the present disclosure, the ABPM can modify an operating mode of the wearable health monitor based on the determined attachment state. Accordingly, instances of the present disclosure can facilitate an ability of the wearable health monitor to operate efficiently and provide reliable data.

FIG. 1 illustrates a patient 10 and an example system 100. The system 100 includes a monitor 102 attached to the patient 10 to detect cardiac activity of the patient 10. The monitor 102 may produce electric signals that represent the cardiac activity in the patient 10. For example, the monitor 102 may detect the patient's heart beating (e.g., using infrared sensors, electrodes) and convert the detected heartbeat into electric signals representing ECG data. The monitor 102 communicates the ECG data to a mobile device 104 (e.g., a mobile phone).

The mobile device 104 may include a program (e.g., mobile phone application) that receives, processes, and analyzes the ECG data. For example, the program may analyze the ECG data and detect or flag cardiac events (e.g., periods of irregular cardiac activity) contained within the ECG data. As noted above, because ECG data may be getting continuously generated, the amount of ECG data can be overwhelming to store and process locally on the mobile device 104. As such, the mobile device 104 can periodically transmit chunks of the ECG data to another device or system, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, in certain instances, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks.

Cardiac Event Server

In the example shown in FIG. 1, the mobile device 104 transmits the ECG data (and associated metadata, if any) to a cardiac event server 106 (hereinafter "the server 106" for brevity); however, the mobile device 104 may communicate directly with the sever 106.

The server 106 includes multiple platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108 (e.g., types of deep neural networks), a cardiac event router 110, a report platform 112, and a notification platform 114. Although only one server 106 is shown in FIG. 1, the server 106 can include multiple separate physical servers, and the various platforms/modules/layers can be distributed among the multiple servers. Each of the platforms/modules/ layers can represent separate programs, applications, and/or blocks of code where the output of one of the platforms/modules/layers is an input to another of the platforms/modules/layers. Each platform/module/layer can use application programming interfaces to communicate between or among the other platforms/modules/layers as well as systems and devices external to the server 106.

The server 106 applies the machine learning model 108 to the ECG data to classify cardiac activity of the patient 10. For example, the machine learning model 108 may compare the ECG data to labeled ECG data to determine which labeled ECG data the ECG data most closely resembles. The labeled ECG data may identify a particular cardiac event, including but not limited to ventricular tachycardia, bradycardia, atrial fibrillation, pause, normal sinus rhythm, or artifact/noise. Further, the labeled ECG data may identify beat classifications such as normal, ventricular, and supraventricular.

If the machine learning model 108 determines that the ECG data most closely resembles a labeled ECG data associated with a cardiac event, then the machine learning model 108 may determine that the patient 10 has experienced that cardiac event. Additionally, the machine learning model 108 may measure or determine certain characteristics of the cardiac activity of the patient 10 based on the ECG data. For example, the machine learning model 108 may determine a heart rate, a duration, or a beat count of the patient 10 during the cardiac event based on the ECG data. The server 106 stores the cardiac event (and associated metadata such as information like beat classification, heart rate, duration, beat count, etc.) in a database for storage. Subsequently, the server 106 may retrieve the cardiac event and associated information from the database.

In certain instances, the mobile device 104 (or monitor 102) may initially classify a cardiac event based on the ECG data. The server 106 may then re-classify or confirm the cardiac event using the machine learning model 108. Doing so allows for a more computationally-expensive analysis of the ECG data to be performed using the computing resources of the server 106, rather than the limited resources of the mobile device 104.

In certain instances, once the ECG data is processed by the machine learning model 108, the ECG data and metadata is made available for the report platform 112. As will be described in more detail below, the report platform 112 can be accessed by a remote computer 116 (e.g., client device such as a laptop, mobile phone, desktop computer, and the like) by a user at a clinic or lab 118.

In other instances, the cardiac event router 110 is used to determine what platform further processes the ECG data based on the classification associated with the cardiac event. For example, if the identified cardiac event is severe, the cardiac event router 110 can flag or send the ECG data, etc., to the notification platform 114. The notification platform 114 can be programmed to send notifications (along with relevant ECG data and associated metadata) immediately to the patient's physician/care group remote computer and/or to the patient 10 (e.g., to their computer system, e-mail, mobile phone application).

Adherence-Based Power Manager

In the example shown in FIG. 1, at least one of the monitor 102, mobile device 104, and/or server 106 can include an adherence-based power manager ("ABPM") 120. In certain instances, the ABPM 120 can be a software application installed on a computing device of at least one of the monitor 102, mobile device 104, and/or server 106. In certain instances, the ABPM 120 can be integrated into one or more software applications installed on at least one of the monitor 102, mobile device 104, and/or server 106 (e.g., the ABPM 120 can be included as a plug-in software component of a software application installed on mobile device 104). The ABPM 120 can include program instructions implemented by a processor, such as a processor of mobile device 104, to perform one or more operations discussed with respect to FIGS. 3 and 4. The ABPM 120 can include modules, such as data manager 125 and device manager 130. In certain instances, data manager 125 and device manager 130 can be integrated into a single module. In certain instances, data manager 125 can include program instructions to perform operations 305-335, FIG. 3 and method 400. In certain instances, device manager 130 can include program instructions to perform operation 340, FIG. 3.

Monitor

Figure 2:
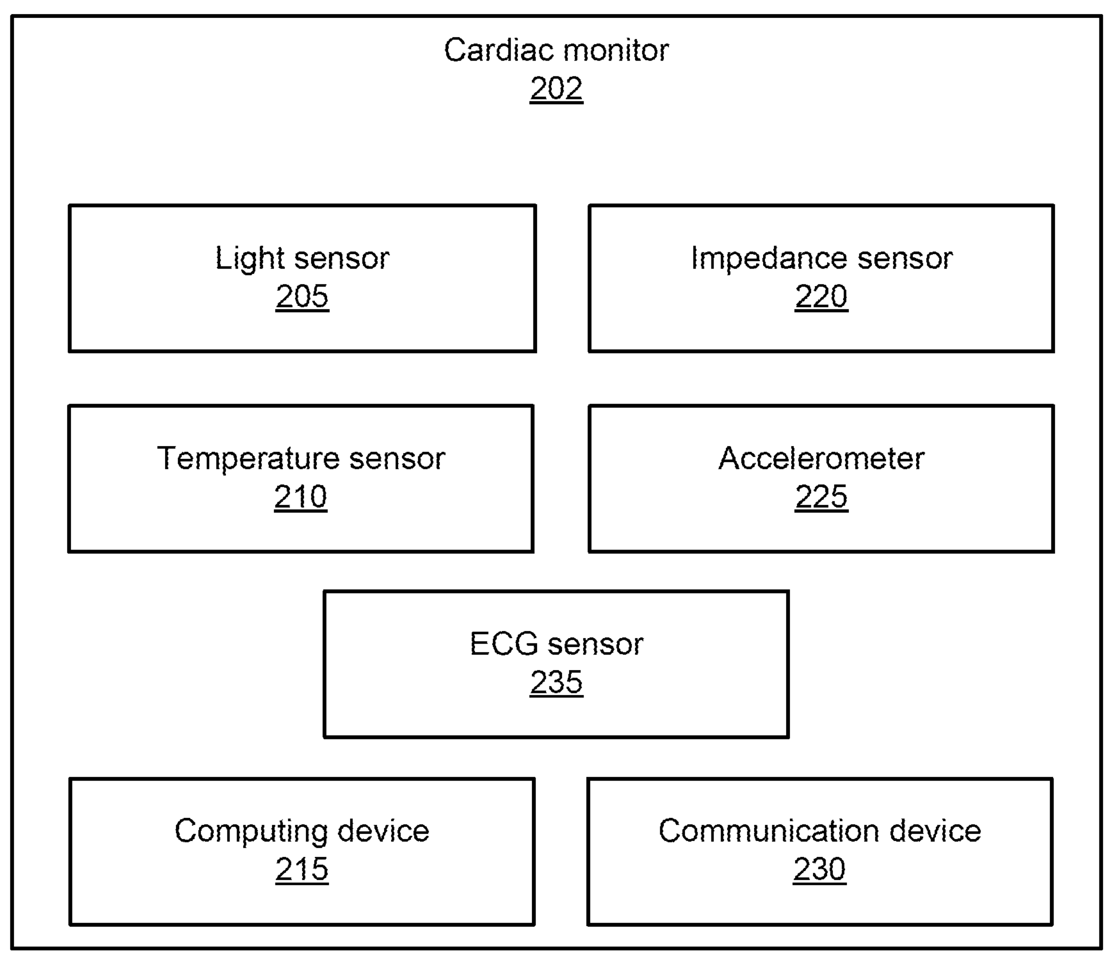
FIG. 2 shows a cardiac monitor, in accordance with certain instances of the present disclosure.

FIG. 2 shows a cardiac monitor 202, in accordance with certain instances of the present disclosure. Cardiac monitor 202 can be identical or substantially similar to monitor 102, FIG. 1 and can be configured to perform one or more operations discussed with respect to FIGS. 3 and 4.

Cardiac monitor 202 can include at least one light sensor 205 (e.g., a Photoplethysmography ("PPG") sensor), temperature sensor 210, computing device 215, impedance sensor 220 (e.g., one or more electrodes), accelerometer 225, ECG sensor 235, and/or communication device 230. In certain instances, computing device 215 can include an ABPM. In certain instances, computing device 215 can be identical or substantially similar to computing device 800, FIG. 8. In certain instances, communication device 230 can permit communication (e.g., wireless data transmission) between the cardiac monitor 202 and a discrete device, such as mobile device 104, FIG. 1.

The cardiac monitor 202 can include a disposable, single-use patch and a reusable monitor. The patch may be positioned on a patient's body (e.g., on the patient's chest), and the monitor may then be engaged to the patch to monitor the patient's cardiac activity and other physiological signals.

Methods

Figure 3:
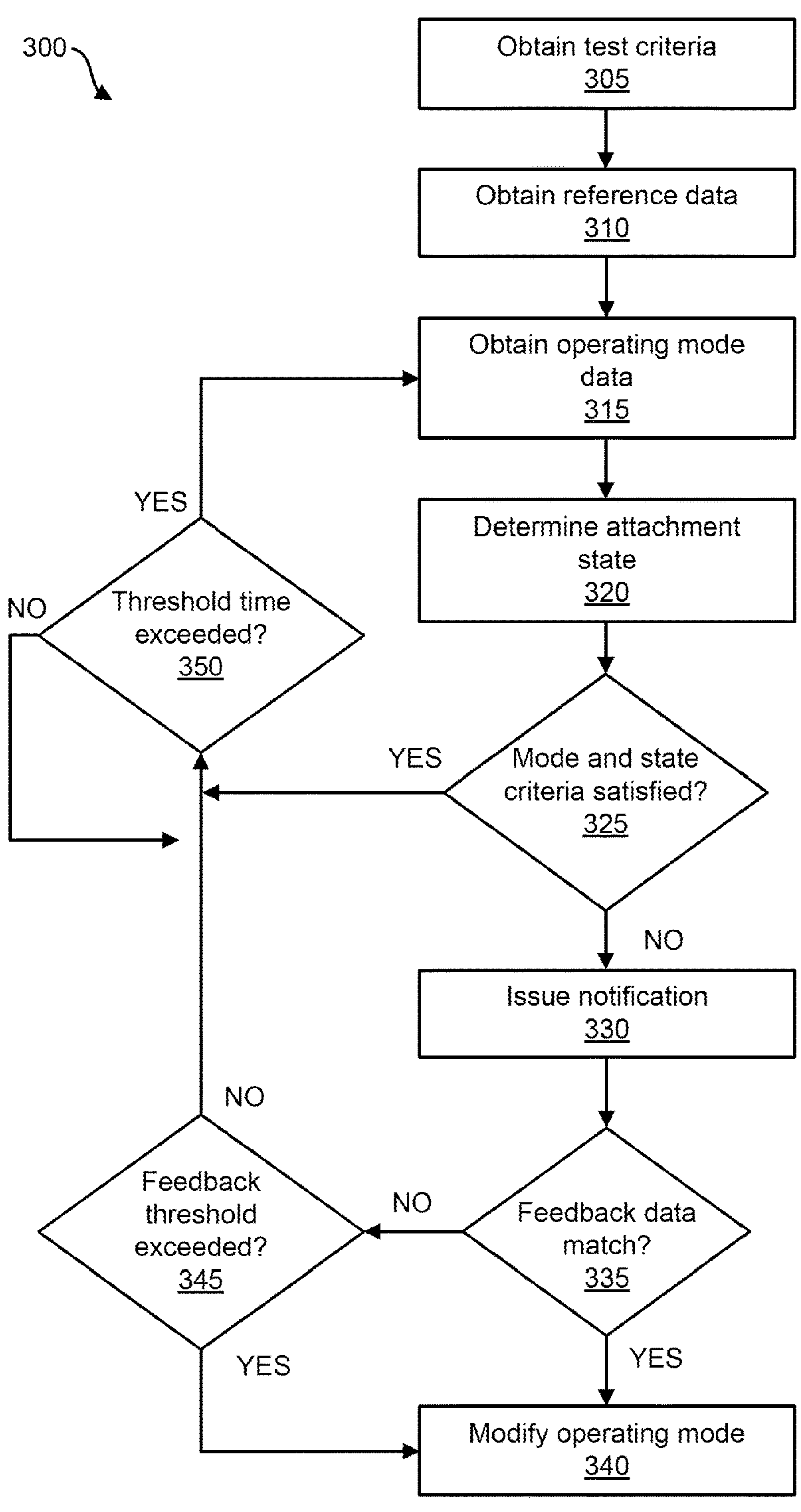
FIG. 3 shows a flow diagram depicting an illustrative method for modifying a cardiac monitor, in accordance with certain instances of the present disclosure.

FIG. 3 shows a flow diagram of an example method 300 for modifying an operating mode of a cardiac monitor, in accordance with certain instances of the present disclosure. Method 300 can be performed by an ABPM, such as ABPM 120 discussed with respect to FIG. 1.

Referring back to FIG. 3, in operation 305, the ABPM obtains test criteria. Test criteria can include information regarding a set of tests to be performed by the ABPM to determine an attachment state of the cardiac monitor. For example, test criteria can include instructions for the ABPM to perform specific tests to determine an attachment state of the cardiac monitor. For example, test criteria can include instructions for the ABPM to perform an impedance test, followed by a temperature test, followed by an R wave test. In this example, the test criteria can further include instructions for the ABPM to determine that the cardiac monitor has a detached state in response to determining in each of the aforementioned tests that the respective threshold is exceeded.

In certain instances, the ABPM can obtain test criteria from a user device, such as mobile device 104, FIG. 1. For example, in certain instances, a user can input test criteria into a user device by a graphical user interface of the user device, and the ABPM can obtain the test criteria as electronic data from the user device. In certain instances, test criteria can include a default set of tests and instructions selected by an entity, such as a programmer of the ABPM. In certain instances, test criteria can be included in program instructions of the ABPM.

In operation 310, the ABPM obtains reference data. Reference data can include one or more thresholds corresponding to operations of method 300, method 400, and/or method 500. For example, reference data can include at least one threshold corresponding to at least one of an impedance, a temperature, an R wave parameter, a heart sound parameter, and/or a PPG parameter. For example, reference data can include a threshold temperature for a temperature test performed by the ABPM. In one example, the threshold temperature can be 36° C. As discussed in more detail below, the ABPM can perform a temperature test to determine whether a temperature measured by the temperature sensor of the cardiac monitor exceeds (e.g., is larger than) 36° C.

In certain instances, the ABPM can obtain reference data from a user device, such as mobile device 104, FIG. 1. For example, in certain instances, a user can input reference data into a user device by a graphical user interface of the user device, and the ABPM can obtain the reference data as electronic data from the user device. In certain instances, reference data can be included in program instructions of the ABPM. In certain instances, the ABPM can obtain reference data from a resource such as a Web server.

In operation 315, the ABPM obtains operating mode data indicating an operating mode of the cardiac monitor. An operating mode can indicate an operating configuration of the cardiac monitor with respect to power consumption and/or data collection. For example, in certain instances, the cardiac monitor can have an active mode and a passive mode. An active mode can include a configuration in which one or more sensors of the cardiac monitor are powered on and are operating to collect data continuously or periodically. In contrast, in certain instances, a passive mode can include a configuration in which the one or more sensors are powered off. In certain instances, a passive mode can include a configuration in which the one or more sensors operate in a low-power mode, such that they do not continuously collect data and/or they collect data less frequently than they would in an active mode (e.g., they collect data intermittently). Accordingly, the cardiac monitor can consume more power in the active mode than it does in the passive mode. In certain instances, the ABPM can obtain the operating mode data from the cardiac monitor. For example, in certain instances, the cardiac monitor can store data indicating its operating mode (e.g., active mode or passive mode) in memory of the cardiac monitor, and the ABPM can obtain such data.

In operation 320, the ABPM determines an attachment state of the cardiac monitor. Determining an attachment state of the cardiac monitor can refer to determining whether the cardiac monitor is attached to a user or detached from a user. For example, the cardiac monitor can have an attached state when the cardiac monitor (e.g., electrodes of the cardiac monitor) is contact with the skin of a user. The cardiac monitor can have a detached state when it is partially or completely removed from the skin of a user. In certain instances, the ABPM can determine the attachment state based on the test criteria obtained in operation 305, the reference data obtained in operation 310, and the operating mode data obtained in operation 315. Methods 400 and 500 outlined in FIG. 4 and FIG. 5, respectively (and discussed in more detail below) are example methods of determining an attachment state in accordance with operation 320.

In operation 325, the ABPM determines whether operating mode and attachment state criteria are satisfied. In certain instances, the operating mode and attachment state criteria can be satisfied based on the ABPM identifying that either (1) the operating mode data indicates that the operating mode of the cardiac monitor is an active mode and the determined attachment state of the cardiac monitor is an attached state or (2) the operating mode data indicates that the operating mode of the cardiac monitor is a passive mode and the determined attachment state of the cardiac monitor is a detached state. In response to determining that the operating mode and attachment state criteria are satisfied, the ABPM proceeds to operation 350. Alternatively, in certain instances, the operating mode and attachment state criteria can be not satisfied based on the ABPM identifying that either (1) the operating mode data indicates that the operating mode of the cardiac monitor is an active mode and the determined attachment state of the cardiac monitor is a detached state or (2) the operating mode data indicates that the operating mode of the cardiac monitor is a passive mode and the determined attachment state of the cardiac monitor is an attached state. In response to determining that the operating mode and attachment state criteria are not satisfied, the ABPM proceeds to operation 330.

In operation 330, the ABPM issues a notification regarding the attachment state of the cardiac monitor. For example, such a notification can include a text message transmitted by the ABPM to a user device (e.g., mobile device 104, FIG. 1). In another example, operation 330 can include the ABPM activating an audible or visible alert from the cardiac monitor. In certain instances, the notification can prompt a response from the user regarding the attachment state. For example, the notification can prompt a user to transmit to the ABPM feedback data indicating whether the cardiac monitor has an attached state or a detached state. In certain instances, the ABPM can use such feedback data to verify the attachment state determined in operation 320. For example, a notification transmitted to a user device can request that a user select a "YES" or a "NO" icon to indicate, respectively, whether the cardiac monitor has an attached state or a detached state. The user device can transmit the feedback data to the ABPM. In certain instances, operation 330 can include the ABPM generating a timestamp indicating a time and/or date when a notification is issued.

In operation 335, the ABPM determines whether, in response to a notification issued in operation 330, it has received feedback data that matches the attachment state determined in operation 320. The ABPM can determine such a match by identifying that (1) both the feedback data and the attachment state determined in operation 320 indicate an attached state or (2) both the feedback data and the attachment state determined in operation 320 indicate a detached state. In response to determining such a match, the ABPM can proceed to operation 340. Alternatively, in response to determining that no feedback data is received or that the feedback data does not match the attachment state determined in operation 320, the ABPM can proceed to operation 345. In certain instances, the ABPM can determine that the feedback data does not match the attachment state determined in operation 320 by identifying that (1) the feedback data and the attachment state determined in operation 320 do not both indicate an attached state or (2) the feedback data and the attachment state determined in operation 320 do not both indicate a detached state.

In operation 345, the ABPM determines whether a feedback threshold is exceeded. A feedback threshold can refer to a threshold regarding a notification issued in operation 330. For example, in certain instances, a feedback threshold can include a predetermined quantity of time, such as a quantity within a range of 5 minutes to 30 minutes. For a case in which the ABPM determined in operation 335 that no feedback data was received, operation 345 can include the ABPM determining whether the difference between a present time and a time when a notification was issued is greater than the feedback threshold. In response to determining that such a difference is greater than the feedback threshold (i.e., determining that the feedback threshold is exceeded), the ABPM can proceed to operation 340. Alternatively, in response to determining that such a difference is less than the feedback threshold (i.e., determining that the feedback threshold is not exceeded), the ABPM can proceed to operation 350. Additionally, for a case in which the ABPM determined in operation 335 that feedback data was received, the ABPM can proceed to operation 350.

In operation 340, the ABPM modifies an operating mode of the cardiac monitor. Such an operating mode can include an active mode and a passive mode. For example, an active mode can include a configuration in which one or more sensors of the cardiac monitor are powered on and are operating to collect data. A passive mode can include a configuration in which the one or more sensors are powered off or in a low-power mode and are not operating to collect data (e.g., not operating continuously). In certain instances, operation 340 can include the ABPM changing the operating mode of the cardiac monitor from an active mode to a passive mode in response to the ABPM determining that the cardiac monitor has a detached state and an active mode. In certain instances, operation 340 can include the ABPM changing the operating mode of the cardiac monitor from a passive mode to an active mode in response to the ABPM determining that the cardiac monitor has an attached state and a passive mode. In certain instances, the ABPM can modify the operating mode of the cardiac monitor by issuing an instruction or command to the cardiac monitor to change a setting of the cardiac monitor from an active mode to a passive mode or from a passive mode to an active mode.

In operation 350, the ABPM can determine whether a threshold time is exceeded. For example, operation 350 can include the ABPM employing a timer to measure an elapsed time. Continuing with this example, the ABPM can compare the elapsed time to a threshold time to determine whether the threshold time is exceeded. In response to determining that the threshold time is exceeded (i.e., determining that the elapsed time is greater than the threshold time), the ABPM can proceed to operation 315. Alternatively, in response to determining that the threshold time is not exceeded (i.e., determining that the elapsed time is not greater than the threshold time), the ABPM can restart the timer and repeat operation 350. In this way, operation 350 can provide a time interval between the ABPM's assessments of the operating mode and attachment state of the cardiac monitor.

Figure 4:
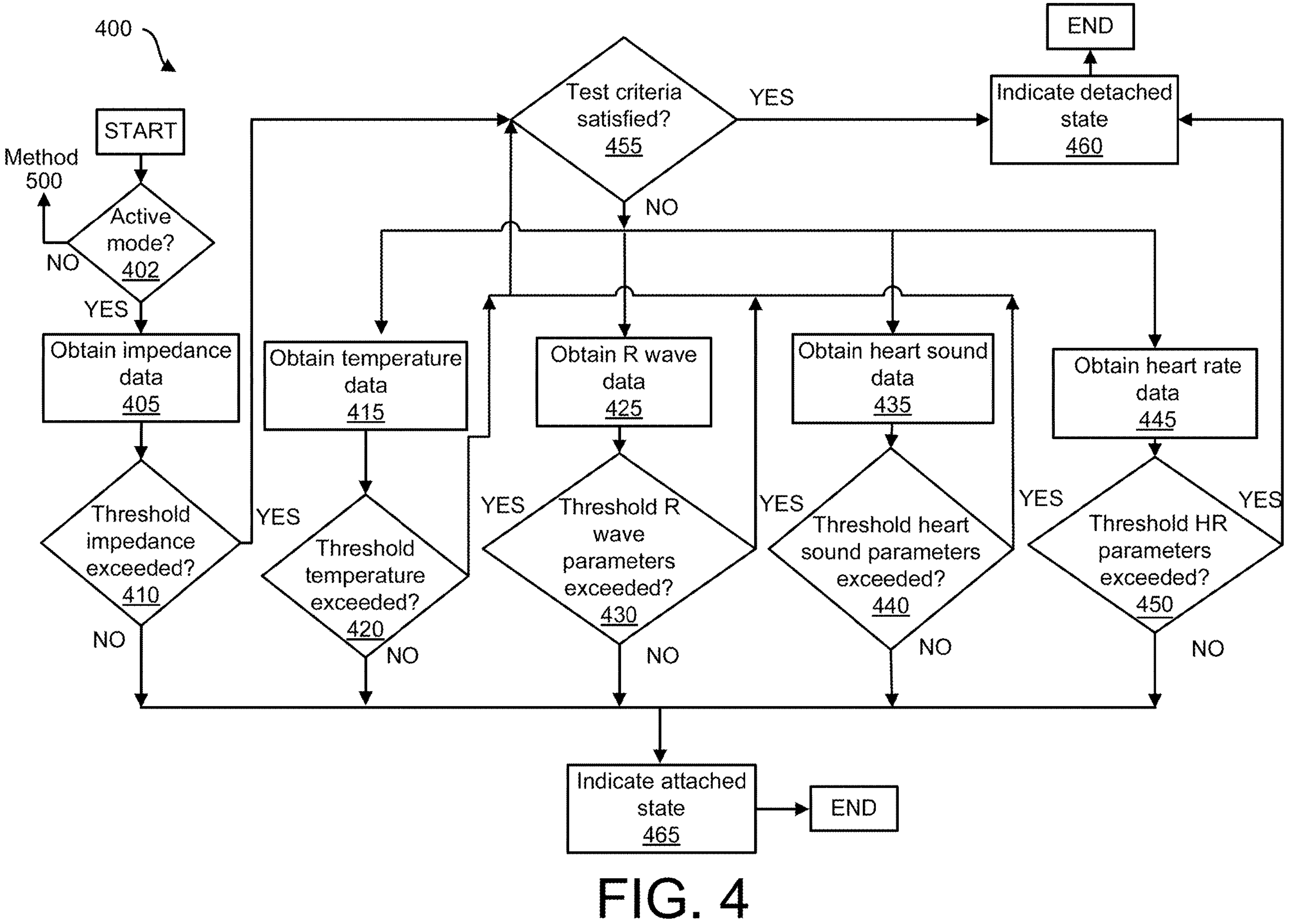
FIG. 4 shows a flow diagram depicting an illustrative method for automatically determining an attachment state of a cardiac monitor in an active mode, in accordance with certain instances of the present disclosure.

FIG. 4 shows a flow diagram of an example method 400 for automatically determining an attachment state of a cardiac monitor in an active mode, in accordance with certain instances of the present disclosure. Method 400 can be performed by an ABPM, such as ABPM 120 discussed with respect to FIG. 1.

In operation 402, the ABPM determines whether the operating mode data obtained in operation 315 indicates an active mode. If the ABPM determines that the operating mode data indicates an active mode, then the ABPM can proceed to operation 405. In certain instances, depending on the test criteria, in response to the ABPM determining that the operating mode data indicates an active mode, the ABPM can alternatively proceed to operation 415, 425, or 435. However, if the ABPM determines that the operating mode data indicates a passive mode, then the ABPM proceeds to method 500.

Method 400 includes a set of five tests that the ABPM can perform to determine an attachment state of the cardiac monitor. The five tests include a first test in which the ABPM analyzes impedance data in operation 410; a second test in which the ABPM analyzes temperature data in operation 420; a third test in which the ABPM analyzes R wave data in operation 430; a fourth test in which the ABPM analyzes heart sound data in operation 440; and a fifth test in which the ABPM analyzes PPG data in operation 450. The ABPM can obtain data for each test, respectively, in operations 405, 415, 425, 435, and 445, respectively. The ABPM can obtain such data from the cardiac monitor.

Regarding the first test, in operation 405, the ABPM obtains impedance data. The ABPM can obtain impedance data from an impedance sensor (e.g., impedance sensor 220, FIG. 2) configured to measure an impedance value. When the cardiac monitor is in the attached state, the impedance value can correspond to a user to whom the cardiac monitor is attached. The impedance data can include a set of impedance values.

Further regarding the first test, in operation 410, the ABPM determines whether a threshold impedance is exceeded. For example, in certain instances, the threshold impedance can be an impedance value within a range of approximately 100 kiloohms to approximately 500 kiloohms. Such a range can correspond to a set of impedance values measured by an impedance sensor when the cardiac monitor is in the attached state. In contrast, in certain instances, when the cardiac monitor is in a detached state, the impedance sensor can measure impedance values that are greater (e.g., 10 times greater) than impedance values measured when the cardiac monitor is in the attached state. In certain instances, the ABPM can determine that the threshold impedance is exceeded by determining that an impedance value obtained in operation 405 is greater than approximately 500 kiloohms or less than approximately 100 kiloohms. If the ABPM determines that the threshold impedance is exceeded, then the ABPM proceeds to operation 455. Alternatively, if the ABPM determines that the threshold impedance is not exceeded, then the ABPM proceeds to operation 465.

Regarding the second test, in operation 415, the ABPM obtains temperature data. The ABPM can obtain temperature data from a temperature sensor (e.g., temperature sensor 210, FIG. 2) configured to measure a temperature value. When the cardiac monitor is in the attached state, the temperature value can correspond to a user to whom the cardiac monitor is attached. The temperature data can include a set of temperature values.

Further regarding the second test, in operation 420, the ABPM determines whether a threshold temperature is exceeded. For example, in certain instances, the threshold temperature can be a temperature value within a range of approximately 32° C. to approximately 40° C. Such a range can correspond to a set of temperature values measured by a temperature sensor when the cardiac monitor is in the attached state. In contrast, in certain instances, when the cardiac monitor is in a detached state, the temperature sensor can measure temperature values that are outside of the aforementioned range. In certain instances, the ABPM can determine that the threshold temperature is exceeded by determining that a temperature value obtained in operation 415 is less than approximately 32° C. or greater than approximately 40° C. If the ABPM determines that the threshold temperature is exceeded, then the ABPM proceeds to operation 455. Alternatively, if the ABPM determines that the threshold temperature is not exceeded, then the ABPM proceeds to operation 465.

Regarding the third test, in operation 425, the ABPM obtains R wave data. The ABPM can obtain R wave data from an ECG sensor (e.g., ECG sensor 235, FIG. 2) configured to measure R wave parameters of a QRS complex. When the cardiac monitor is in the attached state, such R wave parameters can correspond to heart rate information of a user to whom the cardiac monitor is attached. The R wave data can include a set of R wave parameters. In some instances, R wave data can include a plot such as plot 600, FIG. 6.

Further regarding the third test, in operation 430, the ABPM determines whether threshold R wave parameters are exceeded. For example, in certain instances, the threshold R wave parameters can include a heart rate range of approximately 20 beats-per-minute ("BPM") to 170 BPM and an amplitude range of approximately 100 microvolts to approximately 2 millivolts. Such a ranges can correspond to a set of R wave parameters measured by an ECG sensor when the cardiac monitor is in the attached state. In contrast, in certain instances, when the cardiac monitor is in a detached state, the ECG sensor can measure R wave parameters that are outside of the aforementioned ranges. In certain instances, the ABPM can determine that the threshold R wave parameters are exceeded by determining that R wave parameters obtained in operation 425 are outside of the aforementioned ranges. If the ABPM determines that the threshold R wave parameters are exceeded, then the ABPM proceeds to operation 455. Alternatively, if the ABPM determines that the threshold R wave parameters are not exceeded, then the ABPM proceeds to operation 465.

Regarding the fourth test, in operation 435, the ABPM obtains heart sound data. The ABPM can obtain heart sound data from an accelerometer (e.g., accelerometer 225, FIG. 2) configured to measure heart sound parameters. When the cardiac monitor is in the attached state, the heart sound parameters can correspond to a user to whom the cardiac monitor is attached. The heart sound data can include a set of heart sound parameters. In some instances, heart sound data can include a plot such as plot 700 and/or plot 750, FIG. 7.

Further regarding the fourth test, in operation 420, the ABPM determines whether threshold heart sound parameters are exceeded. For example, in certain instances, the threshold heart sound parameters can include (1 milli-g for an S1 heart sound) or amplitude variability in a signal corresponding to heart beat sounds. Such thresholds are discussed further with respect to FIG. 7. If the ABPM determines that the threshold heart sound parameters are exceeded, then the ABPM proceeds to operation 455. Alternatively, if the ABPM determines that the threshold temperature is not exceeded, then the ABPM proceeds to operation 465.

Regarding the fifth test, in operation 445, the ABPM obtains heart rate data. The ABPM can obtain heart rate data from a PPG sensor (e.g., light sensor 205, FIG. 2) configured to measure heart rate data. When the cardiac monitor is in the attached state, such heart rate data can correspond to heart rate information of a user to whom the cardiac monitor is attached. The heart rate data can include a set of heart rate parameters.

Further regarding the fifth test, in operation 450, the ABPM determines whether threshold heart rate parameters are exceeded. For example, in certain instances, the threshold heart rate parameters can include a heart rate range of approximately 20 beats-per-minute ("BPM") to 170 BPM and an amplitude range of approximately 100 microvolts to approximately 2 millivolts. Such a ranges can correspond to a set of heart rate parameters (e.g., R wave parameters) measured by a PPG sensor when the cardiac monitor is in the attached state. In contrast, in certain instances, when the cardiac monitor is in a detached state, the PPG sensor can measure heart rate parameters that are outside of the aforementioned ranges. In certain instances, the ABPM can determine that the threshold heart rate parameters are exceeded by determining that heart rate parameters obtained in operation 445 are outside of the aforementioned ranges. If the ABPM determines that the threshold heart rate parameters are exceeded, then the ABPM proceeds to operation 460. Alternatively, if the ABPM determines that the threshold heart rate parameters are not exceeded, then the ABPM proceeds to operation 465.

Additional details of operations 405, 415, 425, 435, and 445 are provided below. Further, FIGS. 6 and 7 and the descriptions thereof provide additional details about operation 440 in which the ABPM analyzes heart sound data.

The cardiac monitor can employ different sensors to acquire data for each test; thus, the cardiac monitor can consume different quantities of power for each test. For example, in operation 405, the cardiac monitor can consume a first quantity of power to acquire impedance data by an impedance sensor. In operation 415, the cardiac monitor can consume a second quantity of power to acquire temperature data by a temperature sensor. In this example, the second quantity of power can be larger than the first quantity of power. In operation 425, the cardiac monitor can consume a third quantity of power to acquire R wave data. In this example, the third quantity of power can be larger than the second quantity of power. In operation 435, the cardiac monitor can consume a fourth quantity of power to acquire heart sound data by an accelerometer. In this example, the fourth quantity of power can be larger than the third quantity of power. In operation 445, the cardiac monitor can consume a fifth quantity of power to acquire heart rate data by a light sensor. In this example, the fifth quantity of power can be larger than the fourth quantity of power.

Certain instances of the present disclosure can employ tiered testing in which the ABPM performs a sequence of tests to determine an attachment state of the cardiac monitor. Additionally, tiered testing can include the ABPM performing the sequence of tests in order of increasing power consumption by the cardiac monitor. For example, tiered testing can include the ABPM performing the first test described above (i.e., operation 410) prior to performing the second, third, fourth, and fifth tests (i.e., operations 420, 430, 440, and 450, respectively), as the quantity of power consumed by the cardiac monitor for the first test is lower than that consumed by the cardiac monitor for the remaining tests. In another example, tiered testing can include the ABPM performing the third test described above (i.e., operation 430) prior to performing the fifth test (i.e., operation 450), as the quantity of power consumed by the cardiac monitor for the third test is lower than that consumed by the cardiac monitor for the fifth test. In certain instances, the order of testing is predetermined based on power-consumption testing performed and/or analyzed by the manufacturer of the cardiac monitor.

In certain instances, such tiered testing can facilitate an efficient use of power. Such power efficiency can result from the ABPM employing tests in which the cardiac monitor consumes less power (i.e., "lower-power tests") before employing tests in which the cardiac monitor consumes more power (i.e., "higher-power tests"). By employing a lower-power test first, a higher power test can be avoided when the lower-power test indicates that the cardiac monitor has an attached state. Additionally, by performing a plurality of tests to determine a detached state, certain instances of the present disclosure can facilitate accurate determinations of a detached state.

For example, in some instances, test criteria can instruct the ABPM to perform the second, fourth, and fifth tests (i.e., operations 420, 440, and 450, respectively) to determine an attachment state of the cardiac monitor. Continuing with this example, based on the test criteria, the ABPM can begin determining the attachment state by obtaining temperature data from the cardiac monitor in operation 415. Furthermore, if the ABPM determines in operation 420 that the threshold temperature is exceeded, then the ABPM can proceed to operation 465 and indicate an attached state. In that scenario, the fourth and fifth tests, which are higher-power tests relative to the second test, can be avoided, thereby reducing power consumption by the cardiac monitor. Alternatively, if the ABPM determines in operation 420 that the threshold temperature is not exceeded, then the ABPM can proceed to operation 455.

In operation 455, the ABPM can determine that the test criteria is not satisfied, as the fourth and fifth tests are not performed. In response, the ABPM can proceed to operation 435 to obtain heart sound data from the cardiac monitor for the fourth test. In operation 440, if the ABPM determines that the threshold heart sound parameters are exceeded, then the ABPM can proceed to operation 465 and indicate an attached state. In that scenario, the fifth test, which is a higher-power test relative to the fourth test, can be avoided, thereby reducing power consumption by the cardiac monitor. Alternatively, if the ABPM determines in operation 440 that the threshold heart sound parameters are not exceeded, then the ABPM can proceed to operation 455.

In operation 455, the ABPM can determine that the test criteria is not satisfied, as the fifth test is not performed. In response, the ABPM can proceed to operation 445 to obtain data from the cardiac monitor for the fifth test. In operation 450, if the ABPM determines that the threshold PPG parameters are exceeded, then the ABPM can proceed to operation 465 and indicate an attached state. Alternatively, if the ABPM determines in operation 450 that the threshold PPG parameters are not exceeded, then the ABPM can proceed to operation 460 and indicate a detached state. In that scenario, the ABPM completed three different tests that did not indicate an attached state. Accordingly, the repeated result by redundant tests would increase the likelihood that the result was accurate.

Regarding operations 460 and 465, indicating a detached state or an attached state can include the ABPM generating, transmitting, and/or storing data corresponding to the detached state or the attached state.

Figure 5:
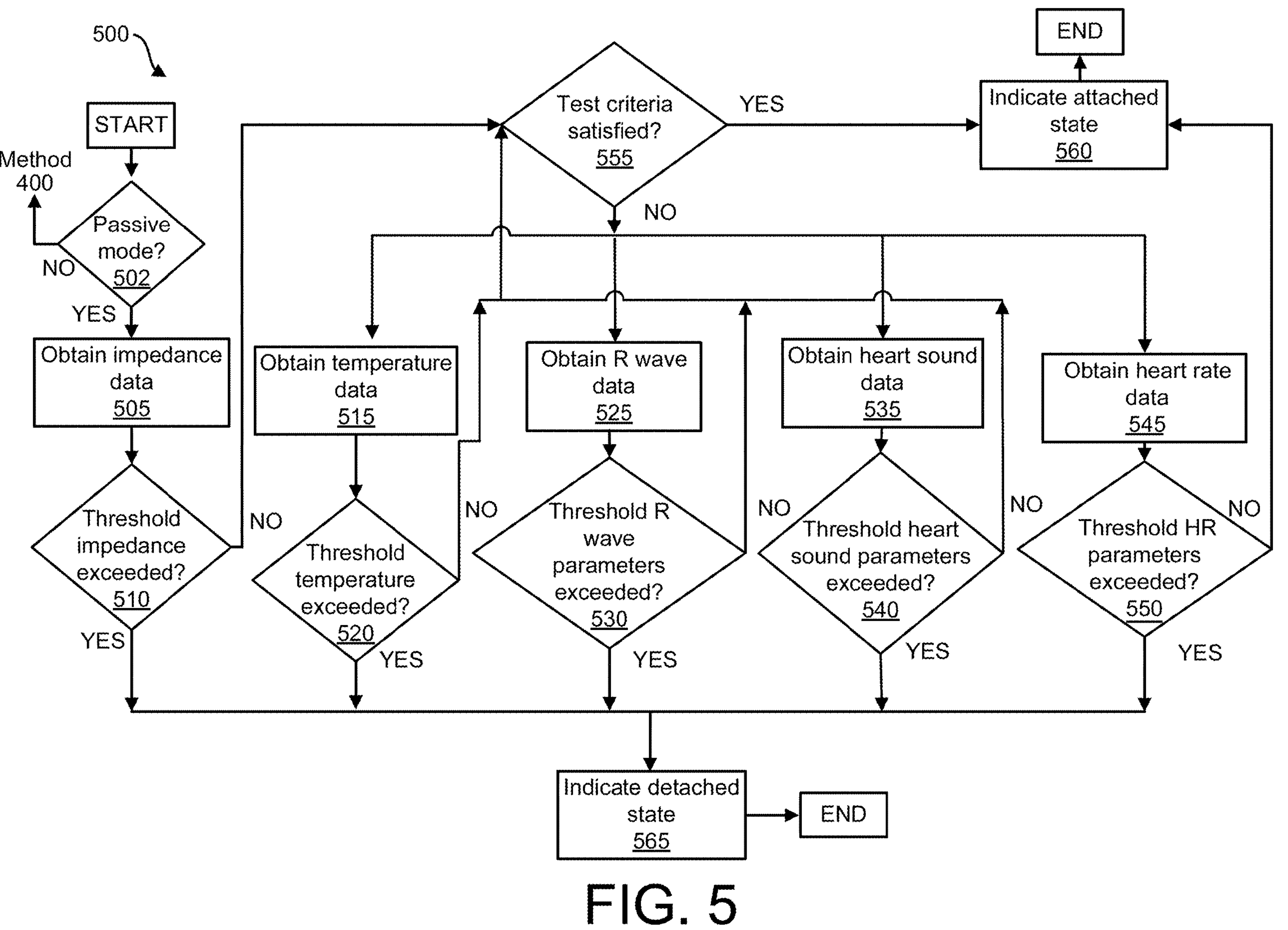
FIG. 5 shows a flow diagram depicting an illustrative method for automatically determining an attachment state of a cardiac monitor in a passive mode, in accordance with certain instances of the present disclosure.

FIG. 5 shows a flow diagram of an example method 500 for automatically determining an attachment state of a cardiac monitor in a passive mode, in accordance with certain instances of the present disclosure. Method 500 can be performed by an ABPM, such as ABPM 120 discussed with respect to FIG. 1.

In operation 502, the ABPM determines whether the operating mode data obtained in operation 315 indicates a passive mode. If the ABPM determines that the operating mode data indicates a passive mode, then the ABPM can proceed to operation 505. In certain instances, depending on the test criteria, in response to the ABPM determining that the operating mode data indicates a passive mode, the ABPM can alternatively proceed to operation 515, 525, or 535. However, if the ABPM determines that the operating mode data indicates an active mode, then the ABPM proceeds to method 400.

The operations of method 500 are analogous to the operations of method 400 having corresponding numbers (e.g., operations 505-555 are analogous to operations 405-455). However, while method 400 can include performing a plurality of tests to indicate a detached state at operation 460, method 500 can include performing a plurality of tests to indicate an attached state at operation 560. Such a configuration permits the ABPM to perform multiple tests before indicating a detached state in the case of a cardiac monitor having an active mode. Such a configuration further permits the ABPM to perform multiple tests before indicating an attached state in the case of a cardiac monitor having a passive mode.

Figure 6:
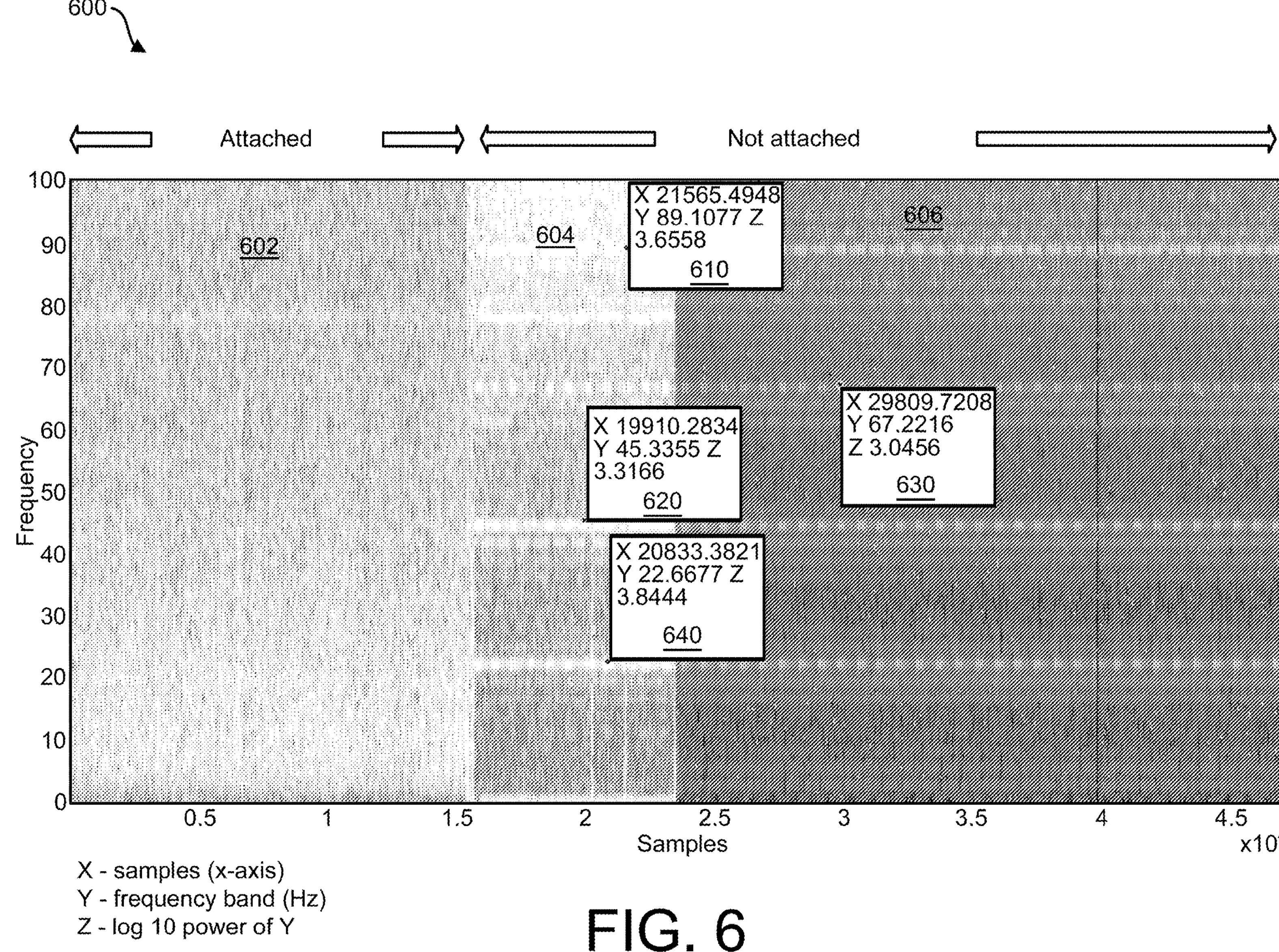
FIG. 6 shows heart rate data, in accordance with certain instances of the present disclosure.

FIG. 6 and the description below provide an example of operation 430 in which the ABPM analyzes heart rate data (e.g., R wave data). The heart rate data can be collected by the ECG sensor 235. The plot 600 of ECG data in FIG. 6 is in the form of an ECG spectrogram, where the frequency content of ECG samples is plotted along the vertical axis.

The first portion 602 of the plot 600 shows an example of the frequency content when a cardiac monitor is properly attached to a patient. The second portion 604 and the third portion 606 of the plot 600 show examples of the frequency content when the cardiac monitor is removed from the patient. When the cardiac monitor is removed, specific frequency tones can be observed within the ECG data. More specifically, noise generated by the cardiac monitor when detached has specific frequency tones that differ from the frequency tones generated by the cardiac monitor when attached to the patient and detecting ECG data.

Regarding FIG. 6, when a cardiac monitor is attached to the body, the ECG shows low frequency activity and some high frequency content, but most of the spectral content is smooth. In contrast to when the device is not attached to the body, spectral tones (i.e. 22 hz and harmonics) can appear in the electrical signal. These tones (e.g., at locations 610, 620, 630, 640) do not reflect physiology as the body is not in contact with the device, but instead reflect signatures of the internal device electronics. The presence of these electrical tones (amplitude of specific frequencies above a baseline value) can indicate that the device is not attached to the body.

Figure 7:
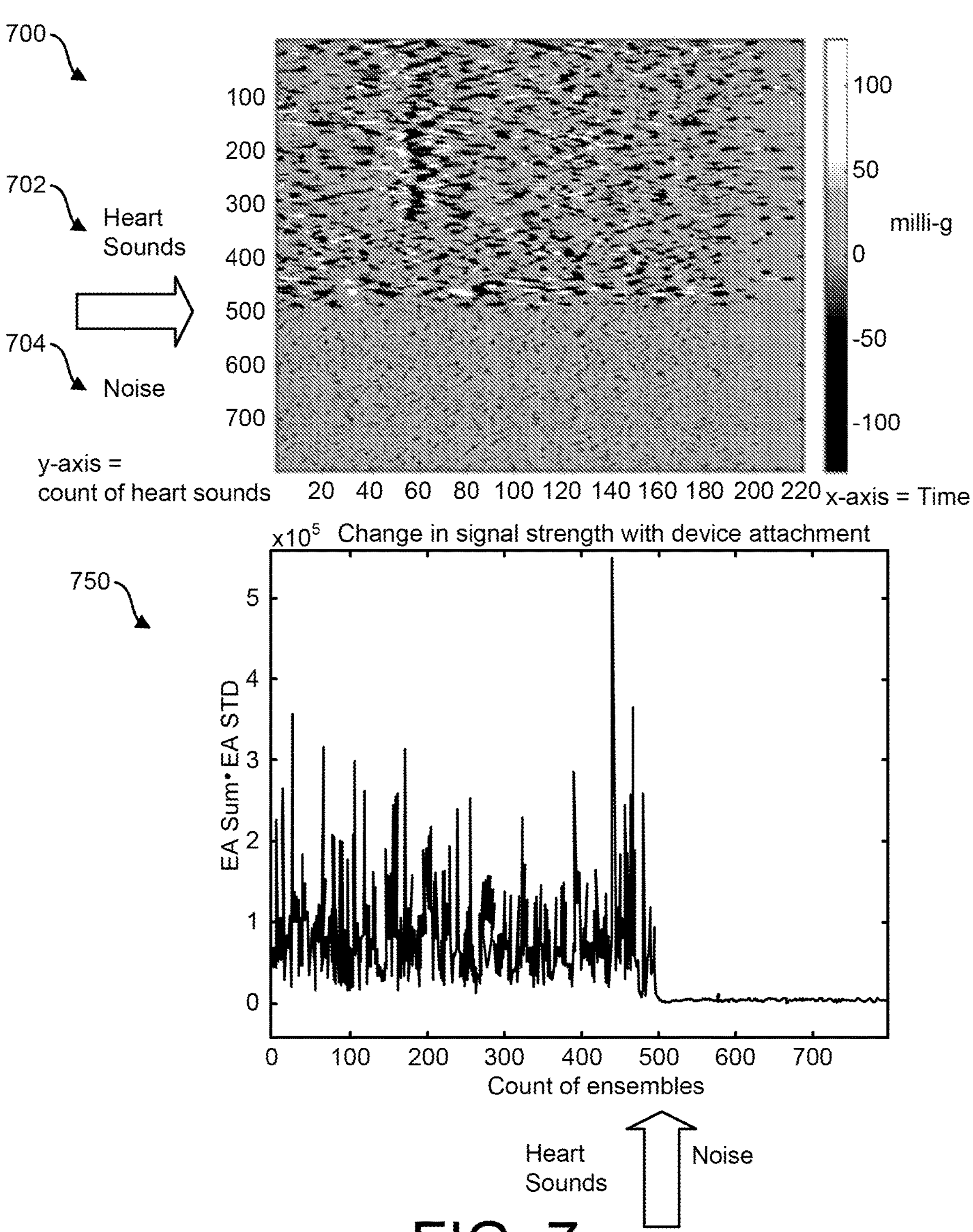
FIG. 7 shows heart sound data, in accordance with certain instances of the present disclosure.

FIG. 7 and the description below provide another example of operation 440 in which the ABPM analyzes heart sound data. The heart sound data can be collected by the accelerometer 225.

Heart sounds are acceleration based signatures of cardiac physiology. When an accelerometer is in contact with the body of a user, the heart sound signal can be observed using an accelerometer. The sensing limit, or noise floor of an accelerometer is the amplitude of acceleration that the accelerometer reports when in still conditions. The amplitude of heart sounds is larger than the noise floor and thus an accelerometer attached to a human body can report an amplitude larger than the noise floor, even if the person is not moving.

A method of determining an attachment state of a cardiac monitor using heart sounds can include comparing an amplitude of an individual heart sound (e.g., an S1, S2, S3, or S4 heart sound) to a noise floor of an accelerometer used to measure the heart sound. In such a method, if the amplitude of the heart sound and the noise floor are substantially similar (e.g., the difference between the amplitude of the heart sound and the noise floor is less than a threshold quantity), then the ABPM can indicate a detached state. In certain instances, the ABPM can indicate a detached state in response to determining that an S1 heart sound is less than 1 milli-g.

An alternate method of determining an attachment state is to compare the amplitude variability, computed as Sum (entire heart sound signal)*standard deviation (entire heart sound signal) (see plot 750, computed from plot 700). During a time when the cardiac monitor has an attached state, a baseline measurement of amplitude variability can be established. A subsequent measurement of amplitude variability that is 3 standard deviations below such a baseline measurement can indicate that the cardiac monitor does not have an attached state; thus, in this case, the ABPM can indicate a detached state.

The plot 700 in FIG. 7 shows signal strength over time, where the signal strength is based on averaging heart sound data. For example, the horizontal axis of the plot represents groups of averaged heart sound data, and the vertical axis represents the signal strength of those groups of averaged data. In certain instances, each group represents 10-60 seconds (e.g., 30 seconds) of heart sound data.

The first portion 702 of the plot 700 shows an example of the signal strength when a cardiac monitor is properly attached to a patient. The second portion 704 of the plot 700 show examples of the signal strength when the cardiac monitor is removed from the patient. As can be seen, once the cardiac monitor is removed, the signal strength of the heart sound data decreases and there is a clear distinction between the attached state and the detached state.

Computing Devices and Systems

Figure 8:
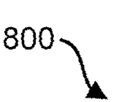
FIG. 8 is a block diagram depicting an illustrative computing device, in accordance with instances of the disclosure.
Figure 8:
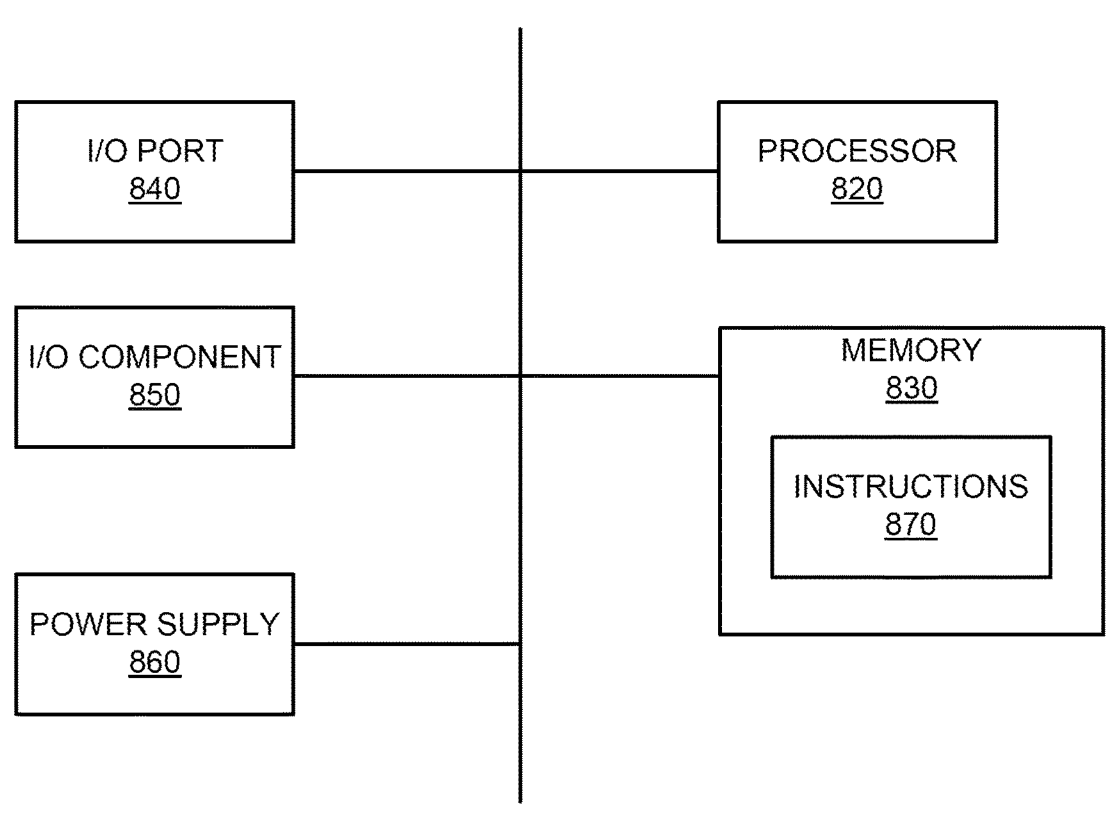

FIG. 8 is a block diagram depicting an illustrative computing device 800, in accordance with instances of the disclosure. The computing device 800 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various components shown and described in the Figures can contain their own dedicated set of computing device components shown in FIG. 8 and described below. For example, the mobile device 104, the server 106, and the remote computer 116 can each include their own set of components shown in FIG. 8 and described below.

In instances, the computing device 800 includes a bus 810 that, directly and/or indirectly, couples one or more of the following devices: a processor 820, a memory 830, an input/output (I/O) port 840, an I/O component 850, and a power supply 860. Any number of additional components, different components, and/or combinations of components may also be included in the computing device 800.

The bus 810 represents what may be one or more busses (such as, for example, an address bus, data bus, or combination thereof). Similarly, in instances, the computing device 800 may include a number of processors 820, a number of memory components 830, a number of I/O ports 840, a number of I/O components 850, and/or a number of power supplies 860. Additionally, any number of these components, or combinations thereof, may be distributed and/or duplicated across a number of computing devices.

In instances, the memory 830 includes computer-readable media in the form of volatile and/or nonvolatile memory and may be removable, nonremovable, or a combination thereof. Media examples include random access memory (RAM); read only memory (ROM); electronically erasable programmable read only memory (EEPROM); flash memory; optical or holographic media; magnetic cassettes, magnetic tape, magnetic disk storage or other magnetic storage devices; data transmissions; and/or any other medium that can be used to store information and can be accessed by a computing device. In instances, the memory 830 stores computer-executable instructions 870 for causing the processor 820 to implement aspects of instances of components discussed herein and/or to perform aspects of instances of methods and procedures discussed herein. The memory 830 can comprise a non-transitory computer readable medium storing the computer-executable instructions 870.

The computer-executable instructions 870 may include, for example, computer code, machine-useable instructions, and the like such as, for example, program components capable of being executed by one or more processors 820 (e.g., microprocessors) associated with the computing device 800. Program components may be programmed using any number of different programming environments, including various languages, development kits, frameworks, and/or the like. Some or all of the functionality contemplated herein may also, or alternatively, be implemented in hardware and/or firmware.

According to instances, for example, the instructions 870 may be configured to be executed by the processor 820 and, upon execution, to cause the processor 820 to perform certain processes. In certain instances, the processor 820, memory 830, and instructions 870 are part of a controller such as an application specific integrated circuit (ASIC), field-programmable gate array (FPGA), and/or the like. Such devices can be used to carry out the functions and steps described herein.

The I/O component 850 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A cardiac monitor comprising:

sensors, wherein the sensors include a cardiac sensor;

a processor; and memory that stores computer-executable instructions for causing the cardiac monitor to:

determine, based on test criteria and reference data, that the cardiac monitor is in a detached state by carrying out (1) a first test corresponding to a first power consumption by the cardiac monitor and (2) a second test different from the first test and corresponding to a second power consumption by the cardiac monitor, the second power consumption being larger than the first power consumption, issue a notification regarding the detached state after the second test is carried out, receive, in response to the notification, a verification of the detached state, and automatically modify, in response to the verification, an operating mode of the cardiac monitor from an active operating mode to a passive operating mode, wherein the passive operating mode reduces power consumption of the cardiac monitor.

2. The cardiac monitor of claim 1, further comprising an impedance sensor, wherein the reference data comprises a threshold impedance, and wherein the first test comprises (1) obtaining impedance data from the impedance sensor, (2) comparing the impedance data to the threshold impedance, and (3) determining that the impedance data is below the threshold impedance.

3. The cardiac monitor of claim 1, further comprising a temperature sensor, wherein the reference data further comprises a threshold temperature, and the second test comprises (1) obtaining temperature data from the temperature sensor, (2) comparing the temperature data to the temperature threshold, and (3) determining that the temperature data is below the temperature threshold.

4. The cardiac monitor of claim 3, wherein the memory further stores computer-executable instructions for causing the processor to carry out a third test corresponding to a third power consumption by the cardiac monitor, wherein the third power consumption is larger than the second power consumption.

5. The cardiac monitor of claim 4, further comprising a light sensor, wherein the reference data comprises threshold PPG data, wherein the third test comprises (1) obtaining PPG data from the light sensor, (2) comparing the PPG data to the PPG threshold, and (3) determining that the PPG data exceeds the PPG threshold, wherein the notification is issued after the determining.

6. The cardiac monitor of claim 1, wherein the reference data comprises threshold R wave data, wherein the second test comprises (1) obtaining R wave data from the cardiac sensor, (2) comparing the R wave data to the R wave threshold, and (3) determining that R wave data exceeds the R wave threshold, wherein the notification is issued after the determining.

7. The cardiac monitor of claim 1, further comprising an accelerometer, wherein the reference data comprises threshold heart sound data, and wherein the second test comprises (1) obtaining heart sound data from the accelerometer of the monitor, (2) comparing the heart sound data to the heart sound threshold, (3) determining that heart sound data exceeds the heart sound threshold, wherein the notification is issued after the determining.

8. The cardiac monitor of claim 7, wherein the heart sound data comprises a signal strength index.

9. The cardiac monitor of claim 1, wherein the active mode comprises powering on one of the sensors, wherein the passive mode comprises powering off the one of the sensors.

10. The cardiac monitor of claim 1, wherein the passive mode comprises reducing a frequency at which data is collected compared to the active mode.

11. The cardiac monitor of claim 1, wherein the notification is a text message.

12. A method comprising:

obtaining test criteria for a monitor configured to be attached to a user;

obtaining reference data;

determining, based on the test criteria and the reference data, a detached state of the monitor;

wherein the determining the detached state comprises performing a set of tests indicated in the test criteria, the set of tests comprising:

a first test corresponding to a first power consumption by the monitor, and a second test different from the first test, the second test corresponding to a second power consumption by the monitor, the second power consumption being larger than the first power consumption;

issuing a notification regarding the detached state after the second test is carried out;

receiving, in response to the notification, a verification of the detached state; and automatically modifying, in response to the verification of the detached state, an operating mode of the monitor from an active mode to a passive mode, wherein the passive operating mode reduces power consumption of the monitor.

13. The method of claim 12, wherein the reference data comprises a threshold impedance, and wherein performing the first test comprises:

obtaining, by an impedance sensor of the monitor, impedance data; and comparing the impedance data to the threshold impedance.

14. The method of claim 13, wherein the reference data further comprises a threshold temperature, and wherein the performing the second test comprises:

obtaining, by a temperature sensor of the monitor, temperature data, and comparing the temperature data to the threshold temperature data.

15. The method of claim 14, wherein the set of tests comprises a third test different from the first test and different from the second test, wherein the third test corresponds to a third power consumption by the monitor, and wherein the third power consumption is larger than the second power consumption.

16. The method of claim 12, wherein the passive mode comprises reducing a frequency at which data is collected compared to the active mode.

17. The method of claim 12, wherein the notification is a text message.

18. The method of claim 12, wherein the notification is an audible alert.

19. The method of claim 12, wherein the notification is an audible alert.

20. The method of claim 12, wherein the passive mode comprises powering off a sensor.

* * * * *